US011735200B2

(12) United States Patent
Mo et al.

(10) Patent No.: US 11,735,200 B2
(45) Date of Patent: Aug. 22, 2023

(54) DUAL-MICROPHONE ADAPTIVE FILTERING ALGORITHM FOR COLLECTING BODY SOUND SIGNALS AND APPLICATION THEREOF

(71) Applicants: SOUTH CHINA UNIVERSITY OF TECHNOLOGY, Guangdong (CN); FOSHAN BAIBUTI MEDICAL TECHNOLOGY CO., LTD., Guangdong (CN)

(72) Inventors: Hongqiang Mo, Guangzhou (CN); Xiang Tian, Foshan (CN)

(73) Assignees: SOUTH CHINA UNIVERSITY OF TECHNOLOGY, Guangzhou (CN); FOSHAN BAIBUTI MEDICAL TECHNOLOGY CO., LTD., Foshan (CN)

( * ) Notice: Subject to any disclaimer, the term of this patent is extended or adjusted under 35 U.S.C. 154(b) by 346 days.

(21) Appl. No.: 17/282,761

(22) PCT Filed: Oct. 10, 2019

(86) PCT No.: PCT/CN2019/110287
§ 371 (c)(1),
(2) Date: Apr. 4, 2021

(87) PCT Pub. No.: WO2020/114071
PCT Pub. Date: Jun. 11, 2020

(65) Prior Publication Data
US 2022/0005491 A1  Jan. 6, 2022

(30) Foreign Application Priority Data
Dec. 6, 2018 (CN) .......................... 201811485004.8

(51) Int. Cl.
G10L 21/0216 (2013.01)
A61B 7/02 (2006.01)
(Continued)

(52) U.S. Cl.
CPC ............ G10L 21/0216 (2013.01); A61B 7/02 (2013.01); H04R 3/005 (2013.01); H04R 3/04 (2013.01); G10L 2021/02165 (2013.01)

(58) Field of Classification Search
CPC ....... G10L 21/0216; G10L 2021/02165; A61B 7/026; A61B 7/02; A61B 7/04; H04R 3/005; H04R 3/04
See application file for complete search history.

(56) References Cited

U.S. PATENT DOCUMENTS

| 2010/0014723 A1 | 1/2010 | Addison et al. | |
| 2016/0015359 A1* | 1/2016 | Emmanouilidou | .... A61B 7/026 600/529 |
| 2018/0317876 A1* | 11/2018 | Emmanouilidou | .... G16H 40/63 |

FOREIGN PATENT DOCUMENTS

| CN | 101763858 | 6/2010 |
| CN | 101763858 A * | 6/2010 |

(Continued)

*Primary Examiner* — Yogeshkumar Patel
(74) *Attorney, Agent, or Firm* — JMB Davis Ben-David

(57) ABSTRACT

The present invention discloses a dual-microphone adaptive filtering algorithm for collecting body sound signals, characterized in that, using at least two microphones, a primary microphone and a secondary microphone, to collect signals; the primary microphone is used to collect noisy body sound signals, and the secondary microphone is used to collect environmental noise; applying a same high-pass filtering to signals collected by the primary microphone and signals collected by the secondary microphone; using a normalized least mean square algorithm on the primary microphone signals and the secondary microphone signals after the high-pass filtering to calculate a weight of the adaptive filter (Continued)

and to calculate an error signal to filter out environmental noise in the primary microphone signals; processing the error signal for a first time by a low-pass filtering to restore the body sound signals, to obtain the body sound signals output by the adaptive filtering algorithm. This algorithm not only may achieve rapid convergence of filter weights, but also avoid signal distortion, and suppress environmental noise interference quickly and reliably.

9 Claims, 6 Drawing Sheets

(51) Int. Cl.
  *H04R 3/00* (2006.01)
  *H04R 3/04* (2006.01)

(56) References Cited

FOREIGN PATENT DOCUMENTS

| | | | | |
|---|---|---|---|---|
| CN | 102347027 | 2/2012 | | |
| CN | 104581516 | 4/2015 | | |
| CN | 106510751 | 3/2017 | | |
| CN | 106691376 | 5/2017 | | |
| CN | 106782593 | 5/2017 | | |
| CN | 108574892 | 9/2018 | | |
| CN | 108574892 A | * | 9/2018 | ............... H04R 1/08 |
| CN | 109545239 | 3/2019 | | |
| WO | 2006081447 | 8/2006 | | |
| WO | 2013055394 | 4/2013 | | |

* cited by examiner

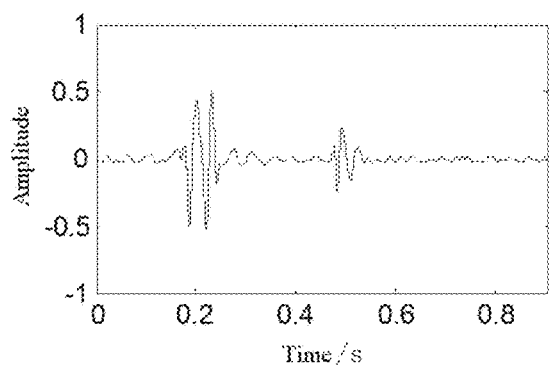
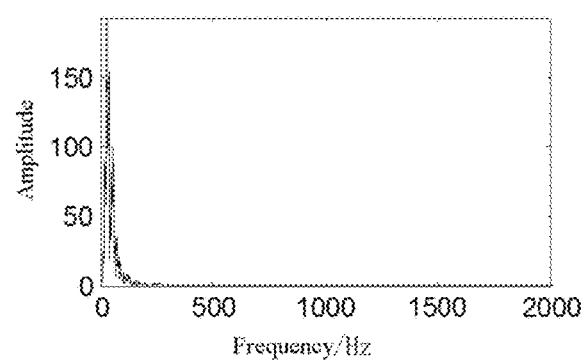
Fig. 3(e)                  Fig. 3(f)
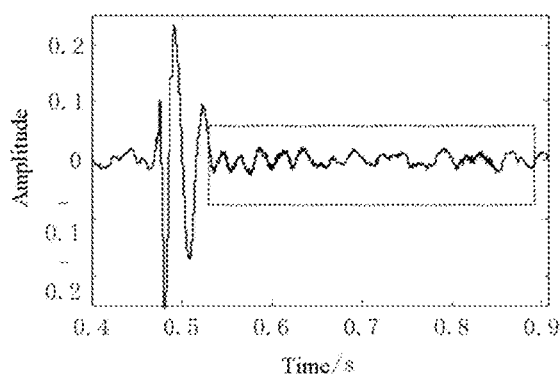
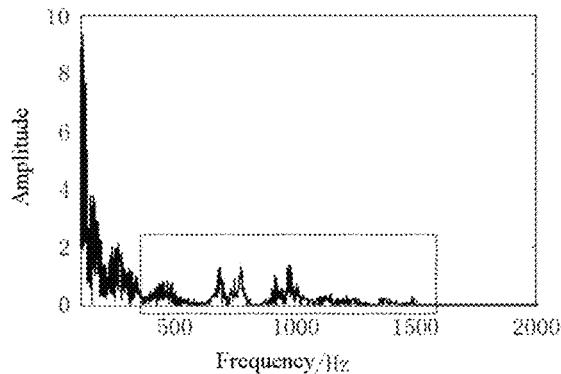
Fig. 4(a)                  Fig. 4(b)
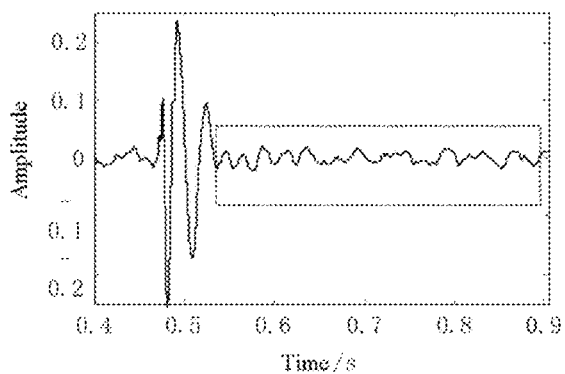
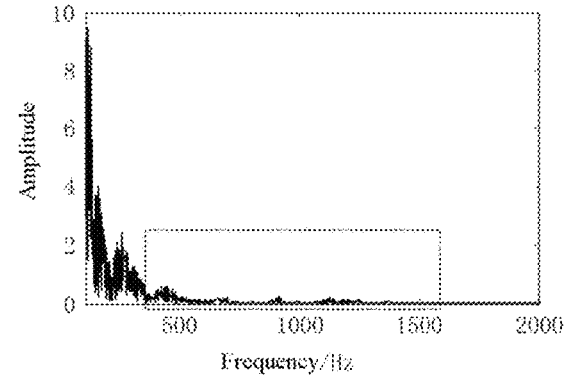
Fig. 4(c)                  Fig. 4(d)

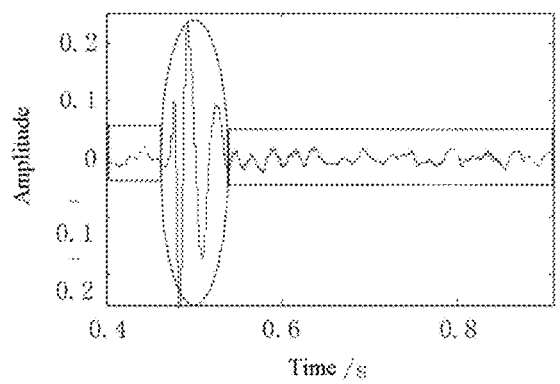
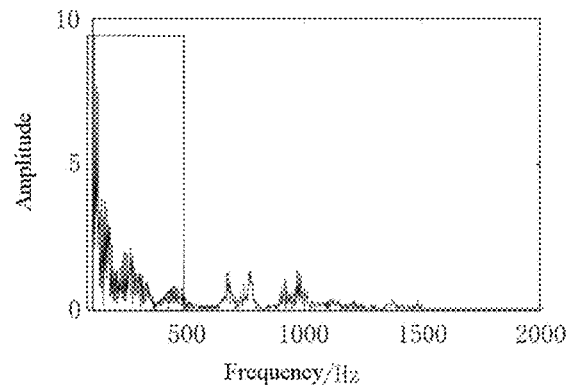
Fig. 5(a)　　　　　　　　　　　Fig. 5(b)
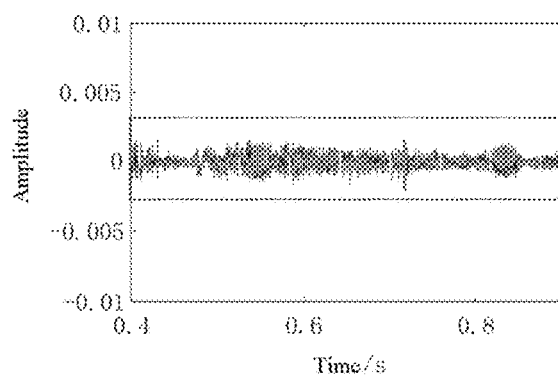
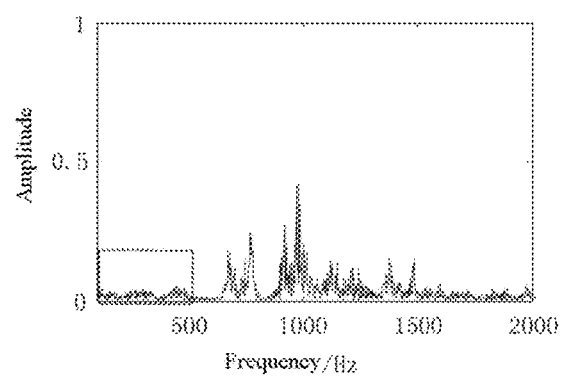
Fig. 5(c)　　　　　　　　　　　Fig. 5(d)
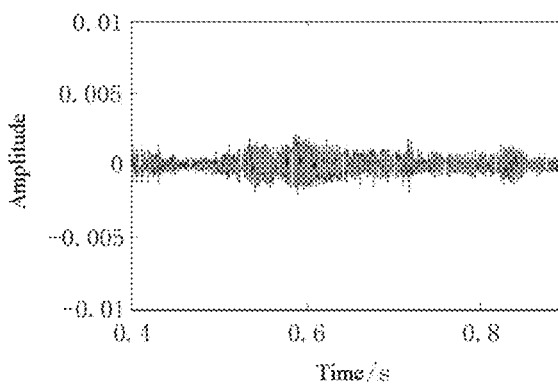
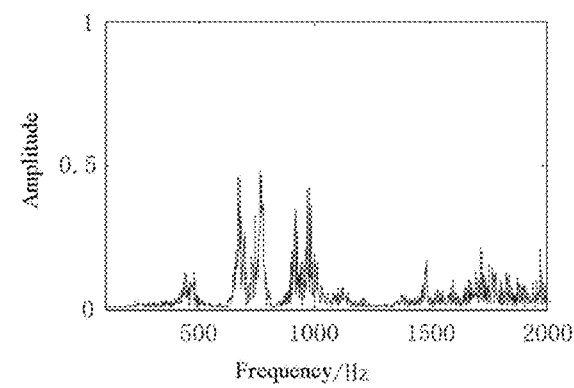
Fig. 5(e)　　　　　　　　　　　Fig. 5(f)

DUAL-MICROPHONE ADAPTIVE FILTERING ALGORITHM FOR COLLECTING BODY SOUND SIGNALS AND APPLICATION THEREOF

CROSS-REFERENCE TO RELATED APPLICATIONS

This is the U.S. National Stage of International Patent Application No. PCT/CN2019/110287 filed on Oct. 10, 2019, which in turn claims the benefit of Chinese Patent Application No. 201811485004.8 filed on Dec. 6, 2018.

TECHNICAL FIELD

The invention relates to the technical field of medical measurements and signal processing, in particular in relation to a dual-microphone adaptive filtering algorithm for collecting body sound signals and application thereof.

TECHNICAL BACKGROUND

Remote auscultation enables users to access remote medical services without leaving home, making it possible to consult a doctor efficiently anytime and anywhere, and greatly reducing the cost of follow-up for patients with chronic diseases. However, remote auscultation has high requirements for anti-noise ability of the auscultation system: weak body sound signals are easily disturbed by environmental noise, and in the process of remote auscultation, doctors do not understand the situation of the patient's environment and therefore, it is difficult to judge whether the abnormal sound heard is the murmur of the patient's body sound or environmental noise, and it is easy to misdiagnose. For this reason, the remote auscultation system must take effective measures to suppress the interference of environmental noise.

A common method is to collect body sound signals with piezoelectric film pickups. Piezoelectric film pickups collect displacement signals, so they are insusceptible to environmental noise. However, in order to ensure sensitivities, the head of the auscultation needs to be designed with a specific structure, and the cost is too high and it is not easy to promote to home users.

One of the preferred sensors for electronic stethoscopes is an electret microphone pickup, which has the advantages of simple structure design, low cost, and wide dynamic range etc. However, an electret microphone is very sensitive. Even if it is encapsulated in a metal cavity, it may collect environmental noise, and a matching filtering method must be designed to be used for remote auscultation. However, the diversity of remote auscultation applications greatly increases the difficulty of the design of the filtering method: the environmental noise is complex and diverse, and its frequency distribution is wide, and it is impossible to model, in particular body sound signals and noise, such as voice and music etc., may overlap in time distribution and frequency band distribution, and it is not easy to perform filtering using traditional filtering methods.

At present, one of the most common methods of filtering environmental noise is dual-microphone adaptive filtering. A primary microphone is used to collect noisy body sound signals. A secondary microphone is used to collect environmental noise. The environmental noise measured by the secondary microphone is linearly processed to offset the noise in the noisy body sound signals to achieve de-noising. A reasonable value of the adaptive step size is the key to ensuring effective adaptive filtering, but its adjustment is often time-consuming, laborious and difficult. At present, the normalized least mean square algorithm is commonly used to set the adaptive step size according to the amplitude of the environmental noise. Usually only a limited number of adjustments are required to adjust the adjustment factor to achieve rapid convergence of filter weights, which greatly reduces the difficulty of adjusting the parameters of the adaptive filtering algorithm.

In the application of the normalized least mean square algorithm, the reasonable value of the adjustment factor $\eta$ is very important: the filter weight iteration depends on the adjustment factor $\eta$: $W(k+1, i)=W(k, i)+\eta(d(k)-y(k))x(k-i)/\varepsilon(k)$; where $d(k)=s(k)+n(k)$, $s(k)$ and $n(k)$ are the body sound signal and environmental noise at the k th time respectively. The output of the adaptive filter is: $e(k)=d(k)-y(k)$. If the adjustment factor is too small, the convergence will be slow, and the purpose of suppressing environmental noise cannot be achieved for a long time. If the adjustment factor is too large, it will easily cause the filter weight $W(k+1, i)$ to be out of adjustment.

If the traditional normalized least mean square algorithm is applied to auscultation filtering, when the amplitude of the body sound signal $s(k)$ is much larger than the amplitude of the environmental noise $n(k)$, the amplitude of the first and second heart sounds is so large that it is easy to cause a mis-adjustment of the adaptive filter parameters, and correspondingly result in output distortion. If a small adjustment factor $\eta$ value is selected in order to reduce the degree of signal distortion, the filter weight will converge too slowly and lose its practical application value. The contradiction between signal fidelity and fast convergence is difficult to overcome by using common normalized least mean square algorithm.

Therefore, the dual-microphone adaptive filtering algorithm still cannot be directly applied to electronic auscultation.

SUMMARY OF THE INVENTION

In order to overcome the shortcomings and deficiencies in the prior art, an object of the present invention is to provide a dual-microphone adaptive filtering algorithm for collecting body sound signals, which may achieve rapid convergence of filter weights, avoid signal distortion, and quickly and reliably suppress environmental noise interference. This algorithm is especially suitable for electronic auscultation. Another object of the present invention is to provide an application of the above dual-microphone adaptive filtering algorithm for collecting body sound signals.

In order to achieve the above objectives, the present invention is implemented through the following technical solutions: A dual-microphone adaptive filtering algorithm for collecting body sound signals, characterized in that, using at least two microphones, a primary microphone and a secondary microphone, to collect signals; the primary microphone is used to collect noisy body sound signals, and the secondary microphone is used to collect environmental noise; applying a same high-pass filtering to signals collected by the primary microphone and signals collected by the secondary microphone, so that primary microphone signals and secondary microphone signals after the high-pass filtering have a good linear correlation; using a normalized least mean square algorithm on the primary microphone signals and the secondary microphone signals after the high-pass filtering to calculate weights of the adaptive filter and to calculate an error signal to filter out environmental noise in the primary microphone signals; processing the error signal for a first time by a low-pass filtering to restore the body sound signals, to obtain the body sound signals output by the adaptive filtering algorithm.

Preferably, the steps of using at least two microphones, a primary microphone and a secondary microphone, to collect signals; the primary microphone is used to collect noisy body sound signals, and the secondary microphone is used to collect environmental noise; applying a same high-pass filtering to signals collected by the primary microphone and signals collected by the secondary microphone, so that primary microphone signals and secondary microphone signals after the high-pass filtering have a good linear correlation; using a normalized least mean square algorithm on the primary microphone signals and the secondary microphone signals after the high-pass filtering to calculate weights of the adaptive filter and to calculate an error signal to filter out environmental noise in the primary microphone signals; processing the error signal for a first time by a low-pass filtering to restore the body sound signals, to obtain the body sound signals output by the adaptive filtering algorithm, means comprising the following steps:

step S1, initializing a current time sequence number k=0, filter weights W(0, i)=0, i=0, ..., M−1, where M is a filter order;

step S2, obtaining the primary microphone signal d(k) and the secondary microphone signals x(k) at the current time;

step S3, judging a size of the current time sequence number k:

if k<M, obtaining signal after the first low-pass filtering as $\bar{e}(k)=d(k)$, and set W(k, i)=W(k−1, i) at the same time, and go to step S10;

if k≥M, go to step S4;

step S4, performing the same high-pass filtering on the primary microphone signals d(k) and the secondary microphone signals x(k) to obtain the primary microphone signal after high-pass filtering $\bar{d}(k)$ and the secondary microphone signal after high-pass filtering $\bar{x}(k)$ to narrow an amplitude gap between the body sound signal and the environmental noise in the primary microphone signals such that the primary microphone signal and the secondary microphone signals after the high-pass filtering have a higher degree of linear correlation;

step S5, calculating a filter output y(k):

$$y(k) = \sum_{i=0}^{M-1} W(k, i)\bar{x}(k-i);$$

step S6, calculating an error signal e(k):

$$e(k)=\bar{d}(k)-y(k);$$

step S7, calculating an adaptive step size normalization coefficient ε(k);

$$\varepsilon(k) = \zeta + \sum_{i=0}^{M-1} \bar{x}^2(k-i);$$

wherein ζ is a positive number to prevent ε(k)=0;

step S8, updating the filter weight W(k+1, i):

$$W(k+1,i)=W(k,i)+\eta e(k)\bar{x}(k-i)/\varepsilon(k);$$

wherein η is an adjustment factor;

step S9, processing the error signal e(k) for the first time by the low-pass filtering to restore the body sound signal, obtaining the signal $\bar{e}(k)$ after the first low-pass filter processing;

step S10, outputting an output signal o(k) of the adaptive filtering algorithm at the k th time; determining an adaptive filtering termination indicator variable: if the adaptive filtering termination indicator variable is true, the adaptive filtering algorithm ends, otherwise jumps to step S2 to calculate an output of the adaptive filtering algorithm of a next time sequence.

Preferably, in step S1, a value range of the filter order M is: M∈[10, 200].

Preferably, in step S4, the high-pass filtering uses one of the following two schemes:

scheme 1: using a high-pass filter with a pulse transfer function of $G_{HP}(z)$, a cut-off frequency $f_{HPc}$ of the pulse transfer function $G_{HP}(z)$ ranges from 500 to 1200 Hz;

scheme 2: using a pre-emphasis high-pass filter formed by $m_{HP}$ first-order pre-emphasis links $1-\alpha_j z^{-1}$, j=1, ..., $m_{HP}$, $\alpha_j \in [0.9, 1)$ in series.

Correspondingly, in the scheme 1, a pulse transfer function of a low-pass filter used in the first low-pass filtering in step S9, $G_{1LP}(z)=1/G_{HP}(z)$.

Preferably, in step S8, a value range of the adjustment factor is: η∈[0.1, 1].

Preferably, in step S10, outputting the output signal o(k) of the adaptive filtering algorithm at the k th time means: using one of the following two methods:

method 1: outputting the signal after the first low-pass filtering $\bar{e}(k)$ as the output signal o(k) of the adaptive filter algorithm at the k th time;

method 2: performing a second low-pass filtering on the signal after the first low-pass filtering $\bar{e}(k)$ to further suppress environmental noise interference, and using a signal after the second low-pass filtering as the output signal o(k) of the adaptive filter algorithm at the k th time.

Preferably, in the method 2, the second low-pass filtering adopts a pulse transfer function of $G_{2LP}(z)$, a cut-off frequency $f_{LPc}$ of the pulse transfer function $G_{2LP}(z)$ ranges from 1200 to 1600 Hz.

An application of the above dual-microphone adaptive filtering algorithm for collecting body sound signals, characterized in that, it is applied to an electronic auscultation device and/or an electronic wearable device, the body sound signals output by the adaptive filtering algorithm is used as output signals of the electronic auscultation device and/or the electronic wearable device. Electronic auscultation devices and/or electronic wearable devices may assist medical personnel in auscultating patients. Electronic auscultation devices may also remotely transmit body sound signals output by adaptive filtering algorithms to the auscultation system. The auscultation system provides the received body sound signal to the medical staff for remote auscultation, and the medical staff may listen to the patient's body sound without meeting with the patient. The technical problem of clear monitoring of body sound is solved for remote medical treatment.

The technical principle of the algorithm of the present invention is:

Compared with the traditional normalized least mean square algorithm, the algorithm of the present invention adds a high-pass filtering and a first low-pass filtering.

In heart sound auscultation, the amplitudes of the first and second heart sounds are often much higher than those of the ambient noise. As a result, the filter deviation e(k)=d(k)−y(k) increases periodically during the convergence of the filter parameters, which in turn causes the filter parameters to be periodically out of adjustment. As shown in FIG. 8(b), the periodic first heart sounds and second heart sounds will cause the filter parameters to be adjusted periodically, wherein the Y-axis in FIG. 8(b) is the adjustment range of the filter weight parameter at the k th time. The adjustment range is measured through the 2 norms of the difference between the filter weight vectors at two adjacent time points, that is $$\|\Delta W(k)\|_2 = \sqrt{\sum_{i=0}^{M-1} [W(k+1, i) - W(k, i)]^2}.$$

Compared with common environmental noises such as voice etc., body sound signals such as heart sounds, breath sounds, and bowel sounds etc. are low-frequency signals, and their effective frequency bands fall from 0 to 1600 Hz, and most of their energy is concentrated in the low frequency band below 500 Hz. The use of high-pass filtering helps to narrow the amplitude gap between the body sound signal s(k) and the environmental noise n(k) in the primary microphone signals. While increasing the influence of environmental noise n(k) on the filter weight W(k+1, i), the influence of body sound signal s(k) on filter weight W(k+1, i) is reduced (compare the amplitudes of $\|\Delta W(k)\|_2$ in FIG. 8(b) and FIG. 8(c)), so as to reduce the output distortion of the adaptive filter, and also to reduce the difficulty of adjusting the adjustment factor η.

The principle may also be explained as: the adaptive filtering uses the linear correlation between the environmental noise x(k) measured by the secondary microphone and the environmental noise n(k) measured by the primary microphone to filter out the environmental noise n(k) in the primary microphone signal. The higher the degree of linear correlation between the two, the more significant suppression effect the adaptive filtering has on environmental noise n(k). Since the body sound signal s(k) is linearly independent of environmental noise n(k), it means that the higher the degree of linear correlation between the secondary microphone signals x(k) and the primary microphone signals d(k)=s(k)+n(k), the better the adaptive filtering effect. High-pass filtering helps to enhance this correlation. The linear correlation coefficient between x̄(k) and d̄(k) may be increased several times or even ten times more than the linear correlation coefficient between x(k) and d(k), which may greatly improve the effect of adaptive filtering.

The purpose of the first low-pass filtering is to restore the body sound signal s(k), so the pulse transfer function of the first low-pass filtering should be the inverse of the pulse transfer function of the high-pass filtering.

Considering that relative to most environmental noise, the body sound signal is a low-frequency signal, after the first low-pass filtering, before the output signal of the adaptive filtering algorithm is obtained, a second low-pass filtering may be introduced to further suppress the interference of environmental noise.

Compared with the prior art, the present invention has the following advantages and beneficial effects:

1. According to the characteristics of the frequency range of the body sound signals, the present invention preprocesses the primary microphone signals and the secondary microphone signals through high-pass filtering to improve the linear correlation between the environmental noise x(k) measured by the secondary microphone and the environmental noise n(k) measured by the primary microphone, and further low-pass filtering the processing results of the normalized least mean square algorithm, to achieve the purpose of quickly and reliably suppressing environmental noise interference. This is especially suitable for the technical field of electronic auscultation;

2. The algorithm of the present invention has a small amount of calculation, and while avoiding signal distortion, the filter has a fast convergence speed, and has low requirements on the computing power of the hardware devices. It is especially suitable for small wearable auscultation equipment and small electronic stethoscopes. At the same time, the algorithm of the present invention is also suitable for application in electronic auscultation auxiliary diagnosis and treatment systems for hospitals and homes.

BRIEF DESCRIPTION OF THE FIGURES

FIGS. 3(a) to 3(f) are comparison diagrams of the amplitude and frequency spectrum of a noisy body sound signal, the noisy body sound signal after high-pass filtering, and the output signal of the adaptive filtering algorithm of the present invention;

FIGS. 4(a) to 4(d) are comparison diagrams of the amplitude and frequency spectrum of a noisy body sound signal before and after adaptive filtering of the present invention;

FIGS. 5(a) to 5(f) are comparison diagrams of the amplitude and frequency spectrum of a noisy body sound signal, the noisy body sound signal after high-pass filtering, and the environmental noise signal measured by the secondary microphone in the present invention;

DETAILED DESCRIPTIONS

The present invention will be further described in detail below with reference to the drawings and specific embodiments.

First Embodiment

Figure 1:
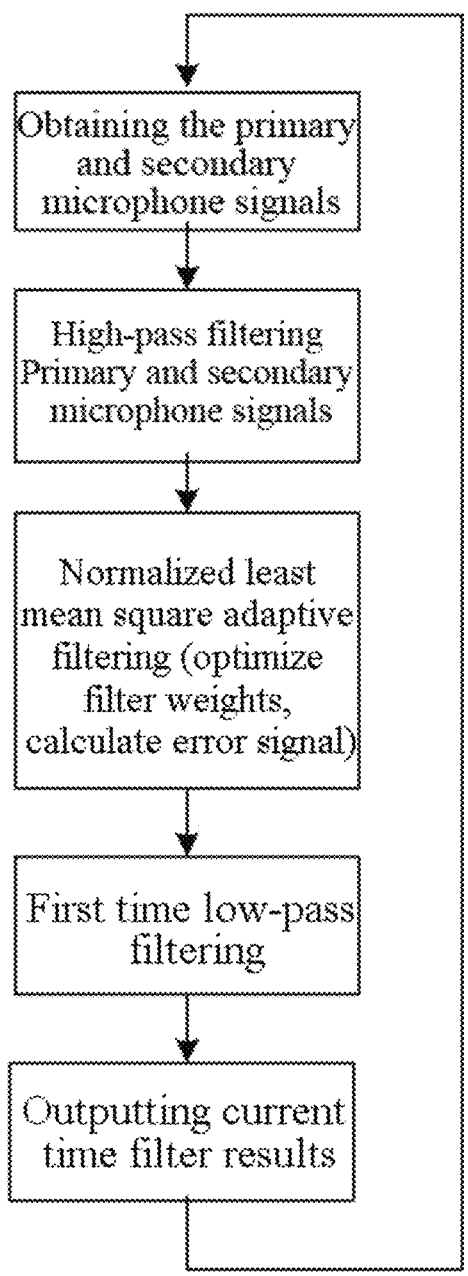
FIG. 1 is a flowchart of the algorithm of the present invention.
Figure 2:
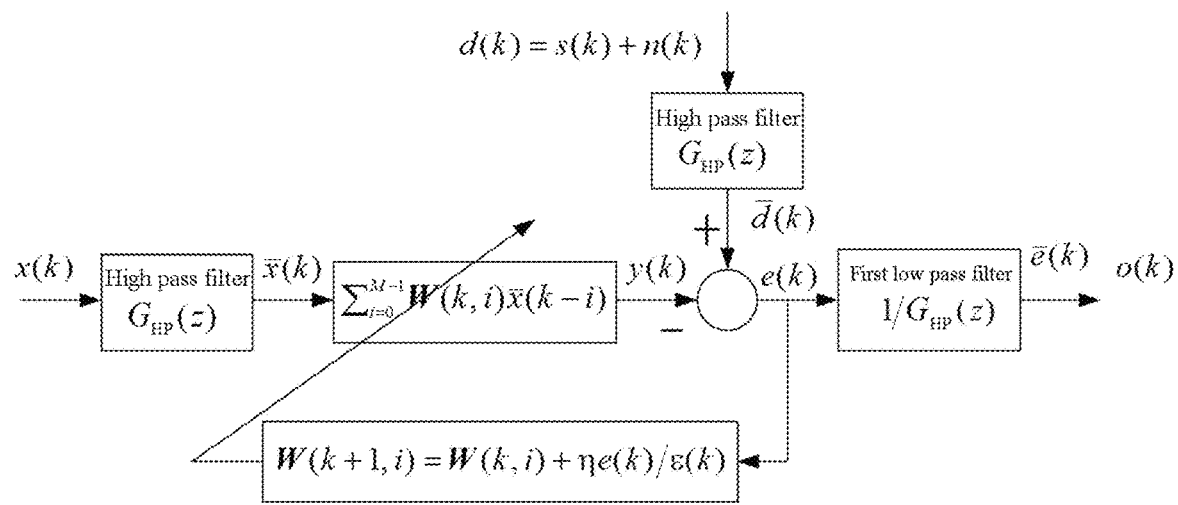
FIG. 2 is a principle diagram of the algorithm of the present invention.

This embodiment is used for the dual-microphone adaptive filtering algorithm for collecting body sound signals, with the flowchart shown in FIG. 1, and the principle diagram shown in FIG. 2, by using at least two microphones, a primary microphone and a secondary microphone, to collect signals; the primary microphone is used to collect noisy body sound signals, and the secondary microphone is used to collect environmental noise; applying a same high-pass filtering to signals collected by the primary microphone and signals collected by the secondary microphone, so that primary microphone signals and secondary microphone signals after the high-pass filtering have a good linear correlation; using a normalized least mean square algorithm on the primary microphone signals and the secondary microphone signals after the high-pass filtering to calculate weights of the adaptive filter and to calculate an error signal to filter out environmental noise in the primary microphone signals; processing the error signal for a first time by a low-pass filtering to restore the body sound signals, to obtain the body sound signals output by the adaptive filtering algorithm.

Specifically, it includes the following steps:

step S1, initializing a current time sequence number k=0, filter weights W(0, i)=0, i=0, . . . , M−1, where M is a filter order; a value range of the filter order M is preferably: M∈[10, 200]

step S2, obtaining the primary microphone signals d(k) and the secondary microphone signals x(k) at the current time;

step S3, judging a size of the current time sequence number k:

if k<M, obtaining signals after the first low-pass filtering as $\bar{e}(k)=d(k)$, and set W(k, i)=W(k−1, i) at the same time, and go to step S10;

if k≥M, go to step S4;

step S4, performing the same high-pass filtering on the primary microphone signals d(k) and the secondary microphone signals x(k) to obtain the primary microphone signals after high-pass filtering $\bar{d}(k)$ and the secondary microphone signal after high-pass filtering $\bar{x}(k)$ to narrow an amplitude gap between the body sound signal and the environmental noise in the primary microphone signal such that the primary microphone signals and the secondary microphone signal after the high-pass filtering have a higher degree of linear correlation;

The high-pass filtering uses one of the following two schemes:

scheme 1: using a high-pass filter with a pulse transfer function of $G_{HP}(z)$, a cut-off frequency $f_{HPc}$ of the pulse transfer function $G_{HP}(z)$ ranges from 500 to 1200 Hz;

scheme 2: using a pre-emphasis high-pass filter formed by $m_{HP}$ first-order pre-emphasis links $1-\alpha_j z^{-1}$, j=1, . . . , $m_{HP}$, $\alpha_j \in [0.9, 1)$ in series.

step S5, calculating a filter output y(k):

$$y(k) = \sum_{i=0}^{M-1} W(k, i)\bar{x}(k-i);$$

step S6, calculating an error signal e(k):

$e(k)=\bar{d}(k)-y(k);$ step S7, calculating an adaptive step size normalization coefficient ε(k);

$$\varepsilon(k) = \zeta + \sum_{i=0}^{M-1} \bar{x}^2(k-i);$$

wherein ζ is a positive number to prevent ε(k)=0, for example, $\zeta=10^{-5}$;

step S8, updating the filter weight W(k+1, i):

$W(k+1,i)=W(k,i)+\eta e(k)\bar{x}(k-i)/\varepsilon(k)$ wherein η is an adjustment factor, a value range of the adjustment factor η is preferably: η∈[0.1, 1];

step S9, processing the error signal e(k) for the first time by the low-pass filtering to restore the body sound signals, obtaining the signal $\bar{e}(k)$ after the first low-pass filter processing;

when the scheme 1 is adopted for the high-pass filtering of step S4, a pulse transfer function of a low-pass filter used in the first low-pass filtering in step S9, is $G_{1LP}(z)=1/G_{HP}(z)$.

step S10, outputting an output signal o(k) of the adaptive filtering algorithm at the k th time after the first low-pass filter processed signal $\bar{e}(k)$; determining an adaptive filtering termination indicator variable: if the adaptive filtering termination indicator variable is true, the adaptive filtering algorithm ends, otherwise jumps to step S2 to calculate an output of the adaptive filtering algorithm of a next time sequence.

An application of the above dual-microphone adaptive filtering algorithm for collecting body sound signals, characterized in that, it is applied to an electronic auscultation device and/or an electronic wearable device, the body sound signals output by the adaptive filtering algorithm is used as output signals of the electronic auscultation device and/or the electronic wearable device. Electronic auscultation devices and/or electronic wearable devices may assist medical personnel in auscultating patients. Electronic auscultation devices may also remotely transmit body sound signals output by adaptive filtering algorithms to the auscultation system. The auscultation system provides the received body sound signal to the medical staff for remote auscultation, and the medical staff may listen to the patient's body sound without meeting with the patient. Thus, the technical problem of clear monitoring of body sounds is solved for remote medical treatment.

The technical principle of the algorithm of the present invention is:

Compared with the traditional normalized least mean square algorithm, the algorithm of the present invention adds a high-pass filtering and a first low-pass filtering.

Figure 8:
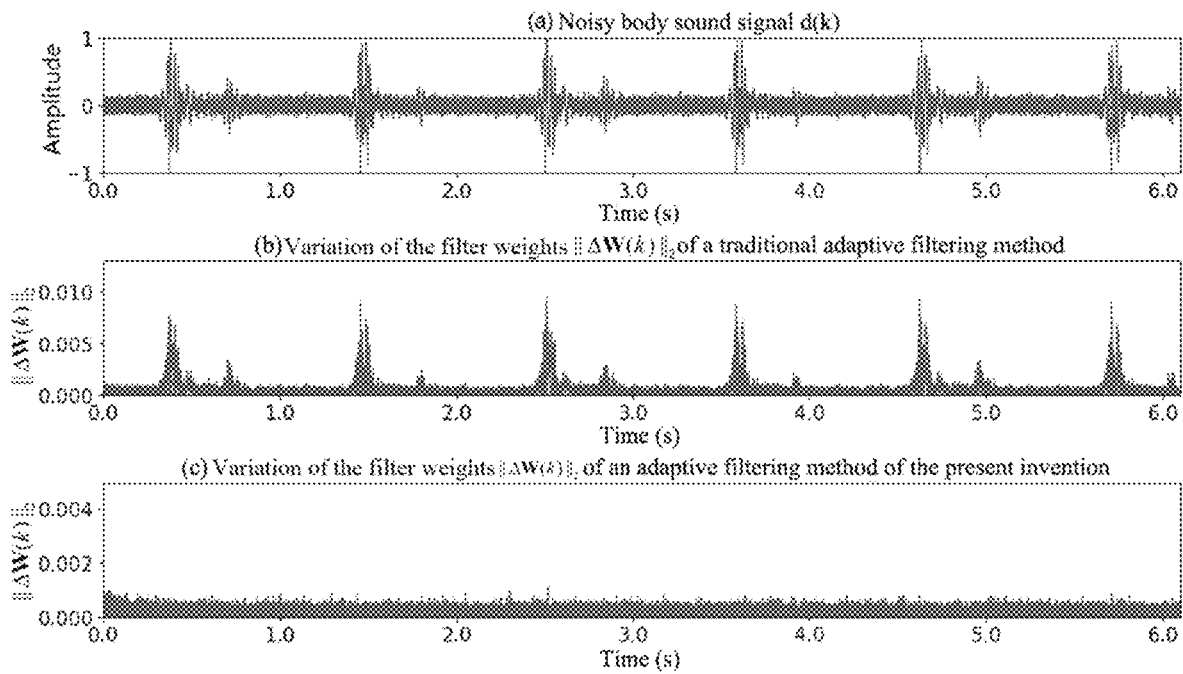
FIGS. 8(a) to (c) are comparison diagrams of the changing curves with respect to time of the filter parameter adjustment range of the noisy body sound signal using the traditional adaptive filtering method, and the changing curves with respect to time of the filter parameter adjustment range of the adaptive filtering method of the present invention.

In heart sound auscultation, the amplitudes of the first and second heart sounds are often much higher than those of the ambient noise. As a result, the filter deviation e(k)=d(k)−y(k) increases periodically during the convergence of the filter parameters, which in turn causes the filter parameters to be periodically out of adjustment. As shown in FIG. 8(b), the periodic first heart sounds and second heart sounds will cause the filter parameters to be adjusted periodically, wherein the Y-axis in FIG. 8(b) is the adjustment range of the filter weights parameter at the k th time. The adjustment range is measured through the 2 norms of the difference between the filter weight vectors at two adjacent time points, that is $$\|\Delta W(k)\|_2 = \sqrt{\sum_{i=0}^{M-1} [W(k+1, i) - W(k, i)]^2}.$$

Compared with common environmental noises such as voice etc., body sound signals such as heart sounds, breath sounds, and bowel sounds etc. are low-frequency signals, and their effective frequency bands fall from 0 to 1600 Hz, and most of their energy is concentrated in the low frequency band below 500 Hz. The use of high-pass filtering helps to narrow the amplitude gap between the body sound signal s(k) and the environmental noise n(k) in the primary microphone signals. While increasing the influence of environmental noise n(k) on the filter weight W(k+1, i), the influence of body sound signal s(k) on filter weight W(k+1, i) is reduced (compare the amplitudes of $\|\Delta W(k)\|_2$ in FIG. 8(b) and FIG. 8(c)), so as to reduce the output distortion of the adaptive filter, and also to reduce the difficulty of adjusting the adjustment factor η.

The principle may also be explained as: the adaptive filtering uses the linear correlation between the environmental noise x(k) measured by the secondary microphone and the environmental noise n(k) measured by the primary microphone to filter out the environmental noise n(k) in the primary microphone signal. The higher the degree of linear correlation between the two, the more significant suppression effect the adaptive filtering has on environmental noise n(k). Since the body sound signal s(k) is linearly independent of environmental noise n(k), it means that the higher the degree of linear correlation between the secondary microphone signals x(k) and the primary microphone signals d(k)=s(k)+n(k), the better the adaptive filtering effect. High-pass filtering helps to enhance this correlation. After using second-order or higher of pre-emphasis process, the linear correlation coefficient between $\bar{x}(k)$ and $\bar{d}(k)$ may be increased several times or even ten times more than the linear correlation coefficient between x(k) and d(k), which may greatly improve the effect of adaptive filtering.

The purpose of the first low-pass filtering is to restore the body sound signal s(k), so the pulse transfer function of the first low-pass filtering should be the inverse of the pulse transfer function of the high-pass filtering.

Figure 3A:
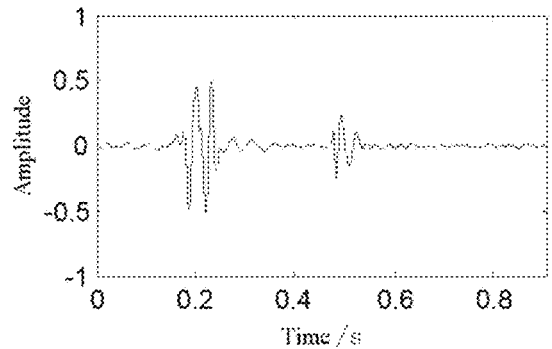
Figure 3B:
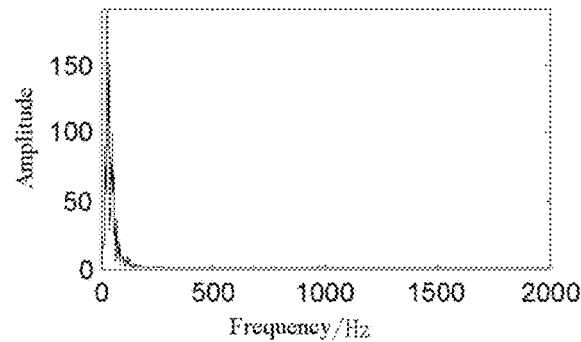
Figure 3C:
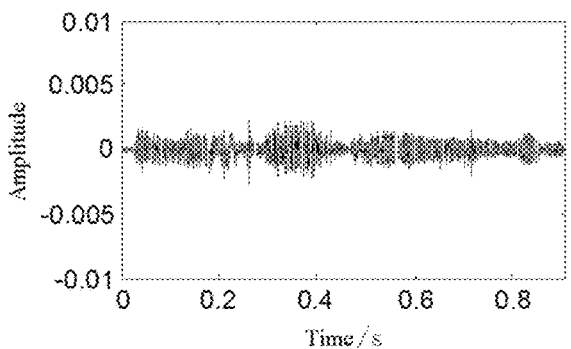
Figure 3D:
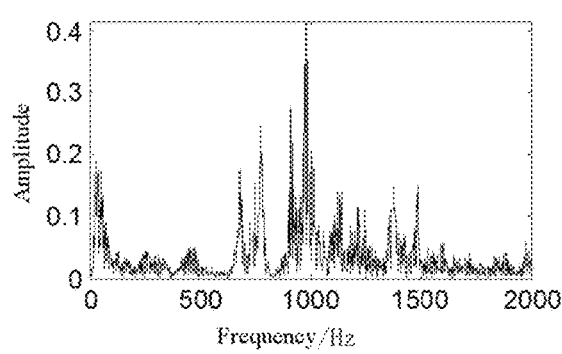

FIGS. 3(a) to 3(f) are comparison diagrams of the amplitude and frequency spectrum of the noisy body sound signal, the noisy body sound signal after high-pass filtering, and the output signal of the adaptive filtering algorithm, wherein FIG. 3(a) is the noisy body sound signal diagram, FIG. 3(b) is the frequency spectrum of the noisy body sound signal, FIG. 3(c) is the noisy body sound signal diagram after high-pass filtering, FIG. 3(d) is the frequency spectrum of the noisy body sound signal after high-pass filtering, FIG. 3(e) is the output signal of the adaptive filtering algorithm, and FIG. 3(f) is the frequency spectrum of the output signal of the adaptive filtering algorithm.

FIGS. 4(a) to 4(d) are comparison diagrams of the amplitude and frequency spectrum of a noisy body sound signal before and after adaptive filtering, wherein FIG. 4(a) is a diagram of noisy body sound signal, FIG. 4(b) is the frequency spectrum of the noisy body sound signal, FIG. 4(c) is the output signal of the adaptive filtering algorithm, and FIG. 4(d) is the frequency spectrum of the output signal of the adaptive filtering algorithm. It can be seen from the figure that the environmental noise is greatly suppressed after adaptive filtering.

FIGS. 5(a) to 5(f) are comparison diagrams of the amplitude and frequency spectrum of a noisy body sound signal, the noisy body sound signal after high-pass filtering, and the environmental noise signal measured by the secondary microphone, wherein FIG. 5(a) is the noisy body sound signal graph, FIG. 5(b) is the frequency spectrum of the noisy body sound signal, FIG. 5(c) is the noisy body sound signal after high-pass filtering, FIG. 5(d) is the frequency spectrum of the noisy body sound signal after high-pass filtering, FIG. 5(e) is the secondary microphone signal after high-pass filtering, and FIG. 5(f) is the frequency spectrum of the secondary microphone signal after high-pass filtering; The figure shows that the low-frequency amplitude of the noisy body sound signal is greatly reduced after high-pass filtering. The primary microphone signals and the secondary microphone signals are more correlated after high-pass filtering, which helps to improve the adaptive filtering effect.

FIGS. 8(a) to (c) are comparison diagrams of the changing curves with respect to time of the filter parameter adjustment range of the noisy body sound signal using the traditional adaptive filtering method, and the changing curves with respect to time of the filter parameter adjustment range of the adaptive filtering method of the present invention, wherein as shown in FIG. 8(b), the amplitude of $\|\Delta W(k)\|_2$ obtained by the traditional adaptive filtering method will periodically change due to the periodic appearance of the first and second heart sounds, resulting in the periodic imbalance of the filter parameters. After adopting the adaptive filtering method of the present invention, the obtained amplitude of $\|\Delta W(k)\|_2$ no longer changes periodically due to the periodic appearance of the first and second heart sounds, which overcomes the phenomenon of periodic imbalance and improves the filter parameter convergence performance.

The following is a specific example for explanation:

The dual-microphone adaptive filtering algorithm for collecting body sound signal comprises the following steps:

step S1, initialization: set the current time sequence number k=0, filter weight W(0, i)=0, i=0, . . . , 19, that is the order of the filter is 20;

step S2, obtaining the primary microphone signals d(k) and the secondary microphone signals x(k) at the current time;

step S3, judging a size of the current time sequence number k: if k<20, obtaining signals after the first low-pass filtering as $\bar{e}(k)$=d(k), and set W(k, i)=W(k−1, i), i=0, . . . , 19 at the same time, and go to step S10; if k≥20, go to step S4;

step S4, performing the same second-order pre-emphasis processing on the primary microphone signal d(k) and the secondary microphone signal x(k) respectively, and the effect is high-pass filtering; that is, the high-pass filtering uses a pre-emphasis high-pass filter formed by two first-order pre-emphasis links $1-\alpha_j z^{-1}$, j=1, 2, $\alpha_j \in$ [0.9, 1) in series;

$\bar{d}(k)=d(k)-(\alpha_1+\alpha_2)d(k-1)+\alpha_1\alpha_2 d(k-2);$ $\bar{x}(k)=x(k)-(\alpha_1+\alpha_2)x(k-1)+\alpha_1\alpha_2 x(k-2);$ where $\alpha_1, \alpha_2 \in$ [0.95, 1);

After the pre-emphasis processing, the linear correlation coefficient between $\bar{x}(k)$ and $\bar{d}(k)$ may be increased several times or even ten times more than the linear correlation coefficient between x(k) and d(k), which may greatly improve the effect of adaptive filtering;

step S5, calculating a filter output $$y(k): y(k) = \sum_{i=0}^{M-1} W(k, i)\bar{x}(k-i);$$

step S6, calculating an error signal e(k):e(k)=$\bar{d}$(k)−y(k);
step S7, calculating an adaptive step size normalization coefficient ε(k);

$$\varepsilon(k) = \zeta + \sum_{i=0}^{M-1} \bar{x}^2(k-i);$$

step S8, updating the filter weight W(k+1, i):

$W(k+1,i)=W(k,i)+\eta e(k)\bar{x}(k-i)/\varepsilon(k);$ step S9, performing de-emphasis processing on the error signal e(k) (that is, the first low-pass filtering) to get $\bar{e}(k)$:

$\bar{e}(k)=e(k)+(\alpha_1+\alpha_2)\bar{e}(k-1)-\alpha_1\alpha_2\bar{e}(k-2);$ step S10, outputting the signal $\bar{e}(k)$ after the first low-pass filtering as the output signal o(k) of the adaptive filtering algorithm at the k th time; determining an adaptive filtering termination indicator variable: if the adaptive filtering termination indicator variable is true, the adaptive filtering algorithm ends, otherwise jumps to step S2 to calculate an output of the adaptive filtering algorithm of a next time. The adaptive filter termination indicator variable is obtained by reading a stop button. When the stop button message is pressed, the adaptive filter termination indicator variable is set to true, otherwise it is set to false.

Second Embodiment

Figure 6:
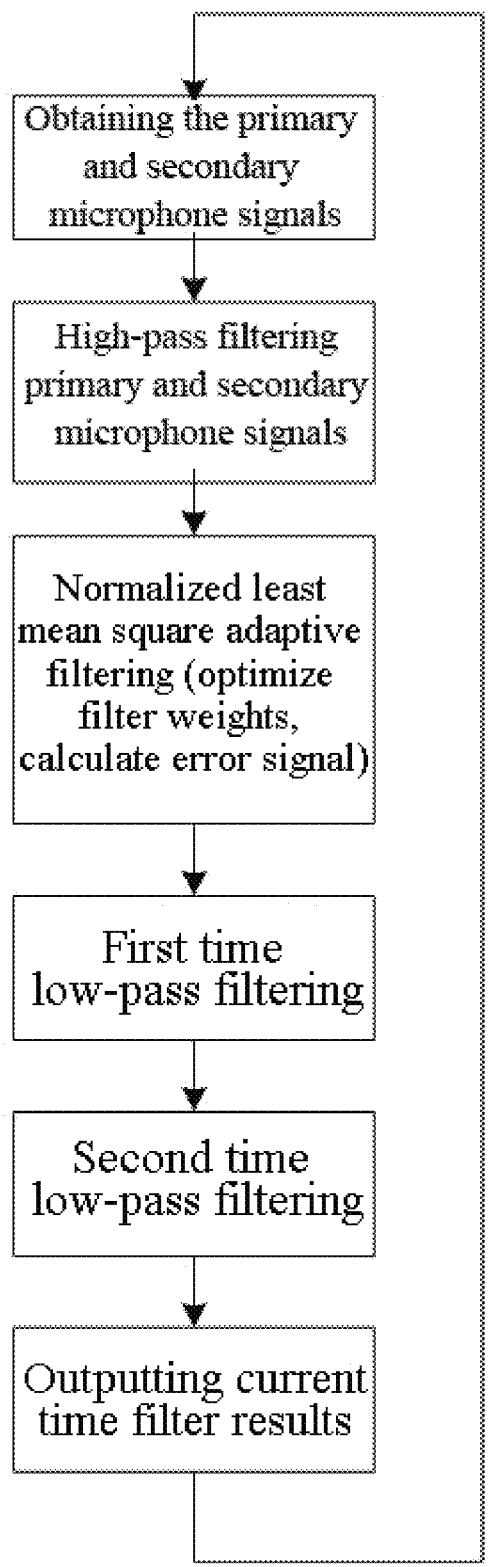
FIG. 6 is the flowchart of the algorithm of the second embodiment.
Figure 7:
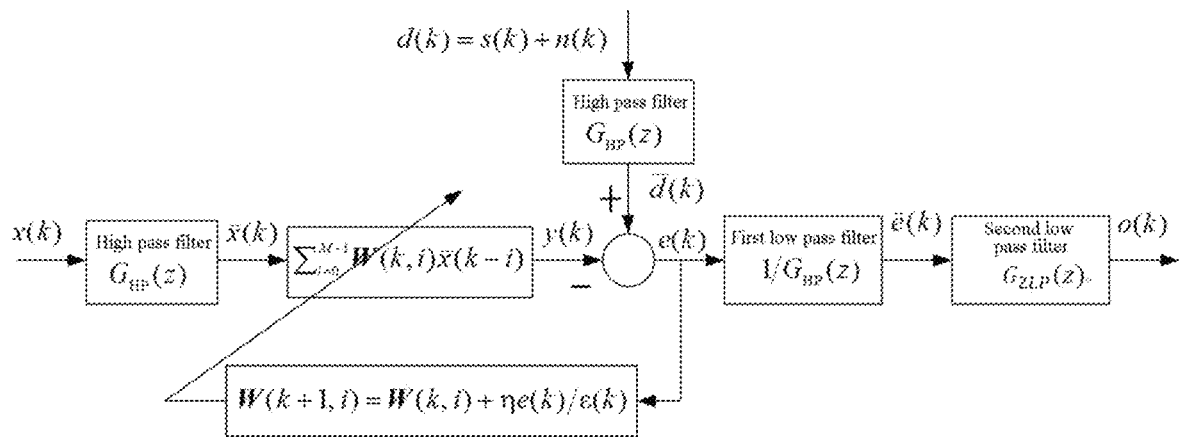
FIG. 7 is the principle diagram of the algorithm in the second embodiment.

This embodiment is used for the dual-microphone adaptive filtering algorithm for collecting body sound signals, with the flowchart shown in FIG. 6, and the principle diagram shown in FIG. 7. The difference from the First Embodiment is that, in this embodiment, in step S10, performing a second low-pass filtering on the signal $\bar{e}(k)$ after the first low-pass filtering to further suppress the environmental noise interference, and outputting the signal after the second low-pass filtering as the output signal o(k) of the adaptive filtering algorithm at the k th time. Considering that relative to most environmental noise, the body sound signal is a low-frequency signal, after the first low-pass filtering, before the output signal of the adaptive filtering algorithm is obtained, the second low-pass filtering may be introduced to further suppress the interference of environmental noise. The remaining steps of this embodiment are the same as the first embodiment.

The second low-pass filtering uses a low-pass filter with pulse transfer function $G_{2LP}(z)$, and the cut-off frequency $f_{LPc}$ of the pulse transfer function $G_{2LP}(z)$ ranges from 1200 to 1600 Hz.

Correspondingly, in a specific example, in step S10, the signal $\bar{e}(k)$ after the first low-pass filtering is low-pass filtered for the second time, and the result is the output signal o(k) of the adaptive filtering algorithm at the k th time:

$o(k)=b_{m_{LP}}\bar{e}(k)+b_{m_{LP}-1}\bar{e}(k-1)+ \ldots +b_0$
$\bar{e}(k-m_{LP}+1)-a_{m_{LP}-1}o(k-1)-a_{m_{LP}-2}o(k-2)- \ldots$
$-a_0 o(k-m_{LP}+1)$ wherein, the order $m_{LP}$ may be selected from 4 to 8 or higher, and the parameters $a_0 \sim a_{m_{LP}-1}$ and $b_0 \sim b_{m_{LP}}$ are determined by the cut-off frequency $f_{LPc}$ (set as 1500 Hz) and the sampling frequency $f_s$ (can be determined by using the Butterworth low-pass filter design algorithm);

After that, determining the adaptive filter termination indicator variable: if the adaptive filter termination indicator variable is true, then the adaptive filter algorithm ends, otherwise jumps to step S2 to calculate the output of the adaptive filter algorithm at the next time.

The remaining steps of this embodiment are the same as the first embodiment.

Third Embodiment

The difference between the dual-microphone adaptive filtering algorithm for collecting body sound signals in this embodiment and the first embodiment is that the steps S4 and S9 in this embodiment are different from the specific example in the first embodiment. In this embodiment, in step S4, the primary microphone signals d(k) and the sub-microphone signals x(k) are subjected to the same high-pass filtering to obtain the primary microphone signals $\bar{d}(k)$ after the high-pass filtering and the secondary microphone signals $\bar{x}(k)$ after the high-pass filtering; the high-pass filtering uses the high-pass filter processor with the pulse transfer function $G_{HP}(z)$. The range of the cut-off frequency $f_{HPc}$ of the pulse transfer function $G_{HP}(z)$ are: 500 to 1200 Hz. For example, the following formulas are used for high-pass filtering:

$\bar{d}(k)=b_{m_{HP}}d(k)+b_{m_{HP}-1}d(k-1)+ \ldots +b_0d(k-m_{HP}+1)-$
$a_{m_{HP}-1}\bar{d}(k-1)-a_{m_{HP}-2}\bar{d}(k-2)- \ldots -a_0$
$\bar{d}(k-m_{HP}+1);$ $\bar{x}(k)=b_{m_{HP}}x(k)+b_{m_{HP}-1}x(k-1)+ \ldots +b_0x(k-m_{HP}+1)-$
$a_{m_{HP}-1}\bar{x}(k-1)-a_{m_{HP}-2}\bar{x}(k-2)- \ldots -a_0$
$\bar{x}(k-m_{HP}+1);$ wherein, the order $m_{HP}$ may be selected from 2 to 8 or higher, and the parameters $a_0 \sim a_{m_{HP}-1}$ and $b_0 \sim b_{m_{HP}}$ are determined by the cut-off frequency $f_{HPc}$ (set as 500 Hz) and the sampling frequency $f_s$ (can be determined by the Butterworth high-pass filter design algorithm). If the passband frequency band gain may be guaranteed to be higher than 20 dB, the effect will be better.

In step S9, performing the first low-pass filtering on the error signal e(k) to obtain the signal $\bar{e}(k)$ after the first low-pass filtering:

$$\bar{e}(k) = \frac{1}{b_{m_{HP}}}[e(k) + a_{m_{HP}-1}e(k-1) + \ldots + a_0 e(k - m_{HP} + 1) - b_{m_{HP}-1}\bar{e}(k-1) - b_{m_{HP}-2}\bar{e}(k-2) - \ldots - b_0\bar{e}(k - m_{HP} + 1)]$$

The remaining steps of this embodiment are the same as the first embodiment.

The above-mentioned embodiments are preferred embodiments of the present invention, but the embodiments of the present invention are not limited by the above-mentioned embodiments. Any other changes, modifications, substitutions, combinations, simplifications, made without departing from the spirit and principle of the present invention, all should be equivalent replacement methods, and they are all included in the protection scope of the present invention.

The invention claimed is:

1. A dual-microphone adaptive filtering algorithm for collecting body sound signals, characterized in that, using at least two microphones, a primary microphone and a secondary microphone, to collect signals; the primary microphone is used to collect noisy body sound signals, and the secondary microphone is used to collect environmental noise; applying a same high-pass filtering to signals collected by the primary microphone and signals collected by the secondary microphone, so that primary microphone signals and secondary microphone signals after the high-pass filtering have a good linear correlation; using a normalized least mean square algorithm on the primary microphone signals and the secondary microphone signals after the high-pass filtering to calculate a weight of the adaptive filter and to calculate an error signal to filter out environmental noise in the primary microphone signals; processing the error signal for a first time by a low-pass filtering to restore the body sound signals, to obtain the body sound signals output by the adaptive filtering algorithm.

2. The dual-microphone adaptive filtering algorithm for collecting body sound signals according to claim 1, characterized in that, the steps of using at least two microphones, a primary microphone and a secondary microphone, to collect signals; the primary microphone is used to collect noisy body sound signals, and the secondary microphone is used to collect environmental noise; applying a same high-pass filtering to signals collected by the primary microphone and signals collected by the secondary microphone, so that primary microphone signals and secondary microphone signals after the high-pass filtering have a good linear correlation; using a normalized least mean square algorithm on the primary microphone signals and the secondary microphone signals after the high-pass filtering to calculate a weight of the adaptive filter and to calculate an error signal to filter out environmental noise in the primary microphone signals; processing the error signal for a first time by a low-pass filtering to restore the body sound signals, to obtain the body sound signals output by the adaptive filtering algorithm, means comprising the following steps:

step S1, initializing a current time sequence number k=0, a filter weight W (0, i)=0, i=0, . . . , −1, where M is a filter order;

step S2, obtaining the primary microphone signals d(k) and the secondary microphone signals x(k) at the current time;

step S3, judging a size of the current time sequence number k:

if k<M, obtaining signals after the first low-pass filtering as $\bar{e}(k)=d(k)$, and set W(k, i)=W(k−1, i) at the same time, and go to step S10;

if k≥M, go to step S4;

step S4, performing the same high-pass filtering on the primary microphone signals d(k) and the secondary microphone signals x(k) to obtain the primary microphone signals after high-pass filtering $\bar{d}(k)$ and the secondary microphone signals after high-pass filtering $\bar{x}(k)$ to narrow an amplitude gap between the body sound signals and the environmental noise in the primary microphone signals such that the primary microphone signals and the secondary microphone signals after the high-pass filtering have a higher degree of linear correlation;

step S5, calculating a filter output y(k):

$$y(k) = \sum_{i=0}^{M-1} W(k, i)x(k-i);$$

step S6, calculating an error signal e(k):

$e(k)=\bar{d}(k)-y(k);$ step S7, calculating an adaptive step size normalization coefficient (k);

$$\varepsilon(k) = \zeta + \sum_{i=0}^{M-1} \bar{x}^2(k-i);$$

wherein ζ is a positive number to prevent ε(k)=0;

step S8, updating the filter weight W(k+1, i):

$W(k+1,i)=W(k,i)+\eta e(k)\bar{x}(k-i)/\varepsilon(k);$ wherein η is an adjustment factor;

step S9, processing the error signal e(k) for the first time by the low-pass filtering to restore the body sound signals, obtaining the signal $\bar{e}(k)$ after the first low-pass filter processing;

step S10, outputting an output signal o(k) of the adaptive filtering algorithm at the k th time; determining an adaptive filtering termination indicator variable: if the adaptive filtering termination indicator variable is true, the adaptive filtering algorithm ends, otherwise jumps to step S2 to calculate an output of the adaptive filtering algorithm of a next time sequence.

3. The dual-microphone adaptive filtering algorithm for collecting body sound signals according to claim 2, characterized in that, in step S1, a value range of the filter order M is: M∈[10, 200].

4. The dual-microphone adaptive filtering algorithm for collecting body sound signals according to claim 2, characterized in that, in step S4, the high-pass filtering uses one of the following two schemes:

scheme 1: using a high-pass filter with a pulse transfer function of $G_{HP}(z)$, a cut-off frequency $f_{HPc}$, of the pulse transfer function $G_{HP}(z)$ ranges from 500 to 1200 Hz;

scheme 2: using a pre-emphasis high-pass filter formed by $m_{HP}$ first-order pre-emphasis links $1-\alpha_j z^{-1}$, j=1, . . . , $m_{HP}$, $\alpha_j \in [0.9, 1)$ in series.

5. The dual-microphone adaptive filtering algorithm for collecting body sound signals according to claim 4, characterized in that, in the scheme 1, a pulse transfer function of a low-pass filter used in the first low-pass filtering in step S9, $G_{1LP}(Z)=1/G_{HP}(z)$.

6. The dual-microphone adaptive filtering algorithm for collecting body sound signals according to claim 2, characterized in that, in step S8, a value range of the adjustment factor is: η∈[0.1, 1].

7. The dual-microphone adaptive filtering algorithm for collecting body sound signals according to claim 2, characterized in that, in step S10, outputting the output signal o(k) of the adaptive filtering algorithm at the k th time means: using one of the following two methods:

method 1: outputting the signal after the first low-pass filtering $\bar{e}(k)$ as the output signal o(k) of the adaptive filter algorithm at the k th time;

method 2: performing a second low-pass filtering on the signal after the first low-pass filtering $\bar{e}(k)$ to further suppress environmental noise interference, and using a signal after the second low-pass filtering as the output signal o(k) of the adaptive filter algorithm at the k th time.

8. The dual-microphone adaptive filtering algorithm for collecting body sound signals according to claim 7, characterized in that, in the method 2, the second low-pass filtering adopts a pulse transfer function of $G_{2LP}(z)$, a cut-off frequency $f_{LPc}$ of the pulse transfer function $G_{2LP}(Z)$ ranges from 1200 to 1600 Hz.

9. An application of the dual-microphone adaptive filtering algorithm for collecting body sound signals according to claim 1, characterized in that, it is applied to an electronic auscultation device and/or an electronic wearable device, the body sound signals output by the adaptive filtering algorithm is used as output signals of the electronic auscultation device and/or the electronic wearable device.

\* \* \* \* \*